United States Patent
Reinhardt

(10) Patent No.: US 9,962,695 B2
(45) Date of Patent: May 8, 2018

(54) COATED CAPILLARY WITH REMELTED COATING FOR FRONT SIDED SEALING

(71) Applicant: AGILENT TECHNOLOGIES, INC., Loveland, CO (US)

(72) Inventor: Thomas Reinhardt, Waldbronn (DE)

(73) Assignee: Agilent Technologies, Inc., Santa Clara, CA (US)

(*) Notice: Subject to any disclaimer, the term of this patent is extended or adjusted under 35 U.S.C. 154(b) by 333 days.

(21) Appl. No.: 14/015,489

(22) Filed: Aug. 30, 2013

(65) Prior Publication Data
US 2013/0334118 A1 Dec. 19, 2013

Related U.S. Application Data

(63) Continuation of application No. PCT/EP2011/053217, filed on Mar. 3, 2011.

(51) Int. Cl.
*B01L 3/00* (2006.01)
*G01N 30/60* (2006.01)

(52) U.S. Cl.
CPC ............ *B01L 3/5027* (2013.01); *B01L 3/561* (2013.01); *B01L 3/565* (2013.01); *G01N 30/6026* (2013.01); *B01L 2300/0838* (2013.01); *B01L 2400/0677* (2013.01); *G01N 30/6095* (2013.01)

(58) Field of Classification Search
CPC .. B01L 3/502; B01L 3/5027; B01L 3/502707; B01L 3/561; B01L 3/565; B01L 2300/0838; G01N 30/6026; G01N 30/6095
See application file for complete search history.

(56) References Cited

U.S. PATENT DOCUMENTS

| | | |
|---|---|---|
| 4,291,903 A | 9/1981 | Fields |
| 6,149,996 A | 11/2000 | Helgerson et al. |
| 6,290,791 B1* | 9/2001 | Shaw ............... B01J 19/0093 156/275.7 |
| 2007/0138076 A1 | 6/2007 | Daridon et al. |

FOREIGN PATENT DOCUMENTS

| | | |
|---|---|---|
| DE | 10356880 | 7/2005 |
| EP | 0636882 | 2/1995 |
| EP | 1457775 | 9/2004 |
| GB | 2486641 | 6/2012 |
| WO | WO8907759 | 8/1989 |
| WO | WO9825065 | 6/1998 |
| WO | WO2007009493 | 1/2007 |

OTHER PUBLICATIONS

Machine translation of EP 1457775, dated Mar. 2, 2004, 6 pages.*
International Search Report and Written Opinion dated Jul. 27, 2011 in Application No. PCT/EP2011/053217.

* cited by examiner

*Primary Examiner* — Katherine Zalasky

(57) ABSTRACT

A method of manufacturing a sealing fluidic component based on a capillary enclosing a fluid conduit and having an exterior surface being at least partially coated with a coating of a meltable material, wherein the method comprises melting the meltable material of the coating at least at an end portion of the capillary, and resolidifying the melted material to thereby form, at the end portion, a sealing integral with the coating and constituted at least partially by the meltable material.

17 Claims, 10 Drawing Sheets

COATED CAPILLARY WITH REMELTED COATING FOR FRONT SIDED SEALING

CROSS-REFERENCE TO RELATED APPLICATION

The present application is a continuation under 35 U.S.C. § 365 of International Patent Application No. PCT/EP2011/053217 filed on Mar. 3, 2011. The entire disclosure of International Patent Application No. PCT/EP2011/053217 is specifically incorporated herein by reference.

BACKGROUND

The present teachings relate to sealing of fluidic components, in particular in a high performance liquid chromatography application.

In high performance liquid chromatography (HPLC), a liquid has to be provided usually at a very controlled flow rate (e.g. in the range of microliters to milliliters per minute or less) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid which may then be identified.

The mobile phase, for example a solvent, is pumped under high pressure typically through a column of packing medium (also referred to as packing material), and the sample (e.g. a chemical or biological mixture) to be analyzed is injected into the column. As the sample passes through the column with the liquid, the different compounds, each one having a different affinity for the packing medium, move through the column at different speeds. Those compounds having greater affinity for the packing medium move more slowly through the column than those having less affinity, and this speed differential results in the compounds being separated from one another as they pass through the column.

The mobile phase with the separated compounds exits the column and passes through a detector, which identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, so called "Internal Band Broadening" or poor system performance, so called "External Band Broadening" are undesirable as they may allow minor components of the mixture to be masked by major components and go unidentified.

During operation, a flow of the mobile phase traverses the column filled with the stationary phase, and due to the physical interaction between the mobile and the stationary phase a separation of different compounds or components may be achieved. In case the mobile phase contains the sample fluid, the separation characteristics is usually configured in order to separate compounds of such sample fluid. The term compound, as used herein, shall cover compounds which might comprise one or more different components. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure occurs across the column.

The flow path of the mobile phase typically comprises plural individual components coupled together, which, in turn, might also be comprised of individual sub-components. Due to the high pressure applied in most HPLC application, pressure sealing of the components in and along the flow path is required. Further, in case of requirement of biocompatibility, it has to be ensured that all surfaces of components (including conduits) along the flow path, which may come in contact with the mobile phase and the sample fluid, are comprised of materials generally considered as being biocompatible, i.e. not to release ions (e.g. from metal parts) which may contaminate the sample and/or a column packaging material, and/or adversely affect the analysis itself. Accordingly, proper sealing is required to ensure such biocompatibility. Sealings should also provide for a small dead volume, low carryover.

However, the requirements regarding sealing performance and mechanical stability of a fluidic component of fluidic measurement devices increases with further increasing operation pressure values.

SUMMARY

According to a representative embodiment of the present invention, a method of manufacturing a sealing fluidic component based on a capillary enclosing a fluid conduit and having an exterior surface being at least partially coated with a coating of a meltable material is provided, wherein the method comprises melting the meltable material of the coating at least at an end portion of the capillary, and resolidifying the melted material to thereby form, at the end portion, a sealing integral with the coating and constituted at least partially by the meltable material.

According to another representative embodiment, a sealing fluidic component is provided which comprises a capillary enclosing a fluid conduit and having an exterior surface being at least partially coated with a coating of a meltable material, and a sealing at an end portion of the capillary integral with the coating, constituted at least partially by the meltable material, and formed by melting the meltable material of the coating at the end portion and resolidifying the melted material.

According to still another representative embodiment, a fluidic device for processing a fluidic sample is provided, wherein the fluidic device comprises a sealing fluidic component having the above mentioned features, and a connector component having a receiving space and a further fluid conduit, wherein the sealing fluidic component and the connector component are configured so that the sealing fluidic component is mechanically receivable or received in the receiving space of the connector component, and wherein the sealing fluidic component and the connector component are configured so that when the sealing fluidic component is mechanically received in the receiving space, the fluid conduit is in fluid communication with the further fluid conduit sealed by the sealing.

According to yet another representative embodiment, a fitting is provided which comprises a sealing fluidic component having the above mentioned features, wherein the fluid conduit of the fitting is in sealed fluid communication with a further fluid conduit of a connector component when the fitting is mechanically received in a receiving space of the connector component.

According to still another representative embodiment, a chromatography device, particularly a HPLC, for separating a fluidic sample is provided, wherein the chromatography device comprises a sealing fluidic component having the above mentioned features, wherein the fluidic sample is to be conducted through the fluid conduit of the sealing fluidic component.

In the context of this application, the term "coated" may particularly denote that the capillary is covered by another material which may be integral with the capillary or which may be separate therefrom, i.e. separable from the capillary.

In the context of this application, the term "end portion" of a capillary may particularly denote a portion of the capillary next to an open end of the capillary at which the fluidic conduit is opened towards an environment. At the open end, the end portion has a flange face which serves for sealing with regard to a counterpart in axial and/or radial direction. The formed sealing may be located at such a flange face and may at least partially cover the flange face.

According to a representative embodiment, a coating on an end portion of a capillary is used to contribute to the formation of a sealing at this end of the capillary. For this purpose, the coating is made of a material which can be melted upon supply of thermal energy. In an embodiment, such a portion of the capillary is supplied with sufficient thermal energy to liquefy or melt the coating material at least locally so that the melted material moves forward to the end portion to form a disk-like seal at this position. In one embodiment, the material of the coating alone forms the seal, whereas in another embodiment, the melted and subsequently solidified material connects in the melted state to another sealing component such as a sealing ring and merges with this separate component to form the sealing. By taking this measure it can be ensured that, when the capillary provided at the end thereof with an integral sealing is connected to another capillary, the (particularly planar) flange face of the sealed capillary can be pressed against a corresponding (particularly flat) surface from which the other capillary or conduit extends from, thereby providing a fluid-tight (particularly high pressure) sealing. The described melting and resolidifying procedure is technically simple and is capable of providing highly reliable sealing performance.

In the following, further embodiments of the method will be explained. However, these embodiments also apply to the sealing fluidic component, the fluidic device, the fitting, and the chromatography device.

In an embodiment, the capillary is integrally coated with the coating. In the context of this application, the term "integrally coated" may particularly denote that the coating is integrally formed with the capillary, i.e. is adhered or otherwise permanently connected to the capillary to thereby form a common single member. In contrast to this, an annular member being slid over the capillary would not be considered as integrally coated. In the described embodiment, the sealing material consists only of a single material, i.e. material of the coating, and has therefore highly homogeneous properties. Therefore, the sealing performance will not change significantly even under the influence of temperature changes or aging effects. For instance, a capillary (for example of fused silica) may be covered by a primary layer (for example of polyimide) which, in turn, may be covered by an actual coating (for example of PEEK or PEKK). The coating may be formed on the capillary (or on the optional primary layer) for instance by extrusion, injection molding, or may be formed as a shrinkage tubing to be shrunk to engage the capillary.

In an embodiment, the coating is provided as at least one annular member being separate from the capillary and being slid over the capillary. Such an embodiment has the advantage that the annular member may be mounted flexibly over the capillary. Thus, a specific annular member may be selected regarding dimension, material, shape to meet specifically requirements of a certain application.

In an embodiment, the method further comprises, between the melting and the resolidifying, guiding at least a part of the melted material forwardly beyond the end portion of the capillary while maintaining a continuous connection between the forwarded material and remaining material of the coating. Consequently, the melted and resolidified material of the coating will extend beyond the flange face of the capillary (and may also move radially outwardly), for instance as a consequence of pressing the melted material in a forward direction or by allowing the material to flow forwardly (for instance under the influence of applied forces and/or the gravity force).

In an embodiment, the method further comprises, prior to the resolidifying, guiding at least a part of the melted material forwardly beyond the end portion to thereby form a disk-like sealing of the forwardly advancing melted material integral with the coating. In such an embodiment, the entire disk-like sealing is formed exclusively by material of the melted coating.

In an embodiment, the method further comprises, prior to the guiding, arranging a molding tool at least around the end portion, the molding tool having a recess defining (partly or entirely) a shape of the disk-like sealing formed within the recess by the forwardly advancing melted material. Providing such a molding tool and placing the molding tool around the end portion allows to properly define the geometry of the disk-like sealing. For example, in case the recess of the molding tool is cylindrical, a (hollow) cylindrical sealing can be formed. In this context, it should be mentioned, that the sealing surface of the disk-like sealing does not have to be completely smooth. It can be patterned by the mold. For instance, formed sealing edges can be advantageous, particularly a plurality thereof, in the form of annular sealing edges.

In an embodiment, the method further comprises arranging a disk-like seal member, being separate from the coating, beside the capillary and in front of the end portion, and prior to the resolidifying, bringing the melted material in contact with the disk-like seal member to thereby form the sealing. In such an embodiment, a disk-like seal member (for instance a seal disk with the Agilent part no. 5043-0257) can be merged with melted and resolidified material of the coating so that both components form the sealing together.

In an embodiment, the method further comprises functionalizing a surface of the disk-like seal member, prior to bringing the melted material in contact with the disk-like seal member, to promote adhesion between the melted material and the disk-like seal member. Such a functionalization may be realized for example by a plasma activation or the like so as to prepare the material of the disk-like seal member for subsequent merging with the melted and resolidified material of the coating.

In an embodiment, the disk-like seal member is made of a material being different from a material of the coating. Thus, the material of the disk-like seal member may be specifically selected to be suitable for sealing purposes. The material of the coating may be specifically selected to be suitable for coating and adhesion purposes. In the described embodiment, a second separate member can be connected by the melting and resolidifying process to be, after resolidifying, integral with the capillary coating.

In an embodiment, the material of the disk-like seal member has a melting temperature higher than a melting temperature of the coating. This ensures that the disk-like seal member is not melted during the merging process, so that its shape remains constant, and nevertheless a reliable connection with the remelted material of the coating is established. Before connecting the two components, the disk-like seal member may be activated, for instance by plasma treatment. This promotes particularly the connectability between PEEK and another for instance inert plastic material.

In an embodiment, the melting is performed at a temperature lower than the melting temperature of the material of the disk-like seal member and higher than the melting temperature of the coating. By taking this measure, it can be ensured that the material of the coating is liquefied and is thermally expanded, so that it has to evade forwardly and therefore flows into the sealing space and connects to the disk-like seal member. For instance, when using PAEK as material of coating or other components, the processing temperatures can range from 350-430° C. The processing temperature may be in a range between 5-20° C. above the melting temperature of the coating.

In an embodiment, the method further comprises, particularly before the melting, arranging a melting heat transfer element, particularly a tubular sleeve, in contact with, particularly around, at least a part of the coating. The term "melting heat transfer element" may denote that this element is configured for transferring melting heat to the meltable material, particularly by heat conduction. The melting heat transfer element, particularly tubular sleeve, may also be denoted as socket and can be a metallic tube which may be slid over the coated capillary. It can be made of steel, particularly of stainless steel or a material having similar properties. For example, titanium is also a suitable choice because it is also chemically inert.

In an embodiment, the method further comprises applying a force or pressure to at least a part of a circumference of the melting heat transfer element, particularly sleeve, to thereby press it onto the coating. The application of force or pressure may be performed by clamping or by crimping the material of the melting heat transfer element, particularly tubular sleeve. Thus, it can be ensured that the sleeve circumferentially engages the capillary with the coating thereon. Since the application of force or pressure around only a part of the circumference may be sufficient, it is also possible to apply the pressure only to one or more axial and/or circumferential segments spaced by gaps. It is also possible to treat the sleeve by rotary swaging along the entire axial extension or only locally. It is also possible to radially press a flaring or a crimp element or to provide one or more recesses or indentations in order to provide for a form closure connection. However, it may be particularly advantageous to have a continuous metal-plastic contact between sleeve and coating along the entire circumference to promote a homogeneous heat transfer. When the coating is made from a plastic material and the sleeve is made from a metal, the thermal expansion of the plastic may be faster than that of the metal so that a potential gap between coating and sleeve can be bridged or at least reduced during heating.

Alternatively, a form closure between sleeve and coating may also be obtained without pressing, for instance when the metal sleeve is patterned or profiled at an inner surface so as to obtain sufficient contact during mounting. For example, this can be achieved by an integrated inner thread or by processing the inner surface so as to form protrusions. A thread can be formed along the entire extension of the sleeve or only at portions thereof, for instance exclusively in a portion directly adjacent to the sealing to be formed. The sleeve can, in such embodiments, be (rotatingly) turned on the coated capillary instead of being slid longitudinally onto the coated capillary. This ensures a proper thermal coupling between coated capillary and sleeve and also increases the effective thermal transfer surface between coated capillary and sleeve as well as promotes a form closure between coated capillary and sleeve.

Melting heat transfer element and disk-like seal member may be integrally formed as one common member. Capillary and coating may be integrally formed as one other common member. In an embodiment, the method further comprises arranging, before the melting, the melting heat transfer element, particularly tubular sleeve, being integrally formed with the disk-like seal member around at least a part of the coating being integrally formed with the capillary. In such an embodiment, it is possible that the disk-like seal member is adhered at a front face of the tubular sleeve so that sleeve and disk-like seal member form one common member. The capillary with the coating may then be inserted into the interior recess of this member so that a front part of the coating will abut against a rear surface of the disk-like seal member. Subsequently heating the coating will then form a properly defined connection between the seal member and the remelted coating.

In an embodiment, the melting heat transfer element, particularly sleeve, comprises a metal, particularly stainless steel. However, other plastically deformable materials are appropriate as well, for instance titanium.

In an embodiment, the method further comprises, prior to the melting, arranging a placeholder in a space at the end portion next to the fluid conduit for maintaining the space free of melted material to thereby establish a fluidic path from the fluid conduit through the free space within the sealing. Such a placeholder ensures that no liquefied material of the coating flows into an area which could close the through-bore in the sealing required for fluid communication between the capillary and a connected fluid conduit. The placeholder can be a cylindrical member, can be formed as a connection of two or more cylinders with different diameters and the same central axis, but can also be a cone or a truncated cone. This member contributes to the shape of the formed sealing, since it keeps the flow path free during the remelting procedure. Advantageous is a design which is free of abrupt changes of the cross-section. This holds particularly for chromatographic applications, since the connection has an influence on the chromatographic performance, peak shape, and carryover properties.

In an embodiment, the melting comprises heating the meltable material to a temperature higher than a melting temperature of the meltable material but below a melting temperature of a material of the capillary. Taking this measure may ensure that the capillary remains in a solid-state during the entire procedure so that particularly any undesired influence on the diameter of the fluid conduit delimited by the capillary can be prevented.

In an embodiment, the melting comprises inductively heating an electrically conductive material thermally coupled to, particularly surrounding, the coating (for instance by inducing eddy currents in the arrangement by coupling a high frequency signal into the arrangement). It is also possible to supply thermal energy to the coating (for instance by placing the arrangement in an oven). It is also possible to irradiate the coating with electromagnetic radiation, particularly infrared radiation (absorption may then result in a heating effect). In an embodiment, the required heat for the remelting procedure can be provided by heating the melting heat transfer element, particularly metallic sleeve. This can be achieved for instance by bringing the melting heat transfer element in direct thermal contact with one or more pre-heated other members. However, it is also advantageous to directly heat the tubular sleeve, for instance by induction, particularly by high frequency induction (for instance in a region of several 100 kHz).

In an embodiment, the sealing is pressed or forced or pushed against a patterned (or profiled) surface portion of a substrate (such as a plate) being at least partially transparent for electromagnetic radiation (such as infrared radiation). Then, the sealing (formed as mentioned above) is irradiated through the patterned surface portion of the substrate with the electromagnetic radiation to thereby remelt material of the scaling so that the remelted material is patterned inversely with respect to the patterned surface portion. Subsequently, the remelted material can be resolidified (for instance by cooling and/or switching off the heating electromagnetic radiation source). In addition to the actual remelting procedure for formation of the sealing, it is also possible by an anew heating of the already formed sealing to pattern a surface of the latter, for example to improve the sealing performance. For instance, a glass plate pressed against the sealing (and having optionally a certain profile on a surface) can be combined with a heating of the sealing area by heat radiation. The thermal energy may be provided by a laser irradiation of the sealing through the glass plate. Pressing the glass plate against the sealing and additional heating can be performed simultaneously. For instance, the heating can be performed by an infrared lamp. Alternatively, a laser can provide the required heat, such as a Nd:YAG laser having a wavelength of 1024 nm.

In an embodiment, the meltable material comprises a plastic, particularly polyaryletherketone, more particularly at least one of the group consisting of polyetheretherketone, polyetherketone, polyetherketoneketone, polyetheretherketoneketone, and polyetherketoneetherketoneketone. Polyaryletherketone (PAEK) is a family of semi-crystalline thermoplastics with high temperature stability and high mechanical strength. PAEK plastics are characterized by phenylene rings that are linked via oxygen bridges (ether and carbonyl groups (ketone)). The ratio and sequence of ether to ketones mainly affect the glass transition temperature and melting point of the polymer. They also affect its heat resistance and processing temperature. The higher the ratio of ketones the more rigid the polymer chain, which results in a higher glass transition temperature and melting point. The processing temperatures can range from 350 to 430° C. Members of the PAEK family include: polyetherketone (PEK), polyetheretherketone (PEEK), polyetherketoneketone (PEKK), polyetheretherketoneketone (PEEKK), and polyetherketoneetherketoneketone (PEKEKK). Polymers of the PAEK family offer a relatively high adhesion behavior to each other, e.g. as apparent from high surface tension (e.g. according to the van OSS method 44.2 mN/m in comparison to PTFE with 18.3 mN/m). The PAEK materials can be or comprise PEK, PEEK, PEKK, PEEKK, PEKEKK. Preferred combinations have been found, for example, in PEEK as the first material and PEK or PEKK as the second material. Suitable PAEK-blends, i.e. blends of PAEK and another material, may also be used, e.g. PEEK-blends of e.g. polyetheretherketone/polyetherimid (PEEK/PEI) may be considered e.g. for the first material.

In an embodiment, the capillary comprises a metal, particularly stainless steel, a plastic, particularly polyetheretherketone or fused silica. Particularly, any material for a capillary is suitable which has a significantly higher melting temperature than the material of the coating, particularly plastic. PEEK which is a suitable plastic material for forming the coating has a melting temperature of 343° C. The capillary can be made of or comprise a metal, stainless steel, titanium, plastic, polymer, ceramic, glass and/or quartz. The capillary may have a lumen having a diameter of less than 0.8 mm, particularly less than 0.2 mm. For instance, the coated capillary together with the tubular sleeve may have an exterior diameter of 1.6 mm or 0.8 mm.

In an embodiment, the sealing fluidic component is configured to be mechanically and fluidically coupled to a correspondingly designed receiving space in a connector component having a further fluid conduit. For instance, the sealing fluidic component may be a fitting to be screwed into a corresponding recess or accommodation space of a housing as the connector component. The term "fitting" shall relate to coupling a fluid conduit (e.g. a tubing) to a fluidic device.

In an embodiment, the fluid conduit has a circular, an elliptical, a polygonal or a rectangular cross section. Other shapes are possible.

In an embodiment, an outer diameter of the coating is in a range between approximately 100 μm and approximately 2000 μm, particularly in a range between approximately 500 μm and approximately 1100 μm, more particularly in a range between approximately 700 μm and approximately 900 μm.

Fluidic devices according to representative embodiments may be particularly suitable for use as fluidic connection pieces for connecting parts of a fluidic instrument such as liquid chromatographic system or the like. For example, columns, fractioners, detectors, or the like of a liquid chromatography apparatus may be connected by such fluidic conduits.

The fluidic device may comprise a processing element filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of the above with a chemically modified (coated, capped, etc.) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 μm to essentially 50 μm. Thus, these beads may be small particles which may be filled inside the separation section of the microfluidic device. The beads may have pores having a size in the range of essentially 0.01 μm to essentially 0.2 μm. The fluidic sample may be passed through the pores, wherein an interaction may occur between the fluidic sample and the pores.

The fluidic device may be configured as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass through the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and analyzed.

The processing element may be a chromatographic column for separating components of the fluidic sample. Therefore, representative embodiments may be particularly implemented in the context of a liquid chromatography apparatus. The processing element may be a trap column. The processing element may be a tubular column or a flat column.

The fluidic device may be configured to conduct a liquid mobile phase through the processing element and optionally a further processing element. As an alternative to a liquid mobile phase, a gaseous mobile phase or a mobile phase including solid particles may be processed using the fluidic device. Also materials being mixtures of different phases (solid, liquid, gaseous) may be processed using representative embodiments.

The fluidic device may be configured to conduct the mobile phase through the system with a high pressure, particularly of at least 600 bar, more particularly of at least 1200 bar (for instance up to 2000 bar).

The fluidic device may be configured as a microfluidic device. The term "microfluidic device" may particularly denote a fluidic device as described herein which allows to convey fluid through microchannels having a dimension in the order of magnitude of less than 500 μm, particularly less than 200 μm, more particularly less than 100 μm or less than 50 μm or less (for instance down to 15 μm or 12 μm). The analysis system may also be configured as a nanofluidic device. The term "nanofluidic device" may particularly denote a fluidic device as described herein which allows to convey fluid through nanochannels with a flow rate of less than 100 nl/min, particularly of less than 10 nl/min.

BRIEF DESCRIPTION OF THE DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

Figure 1:
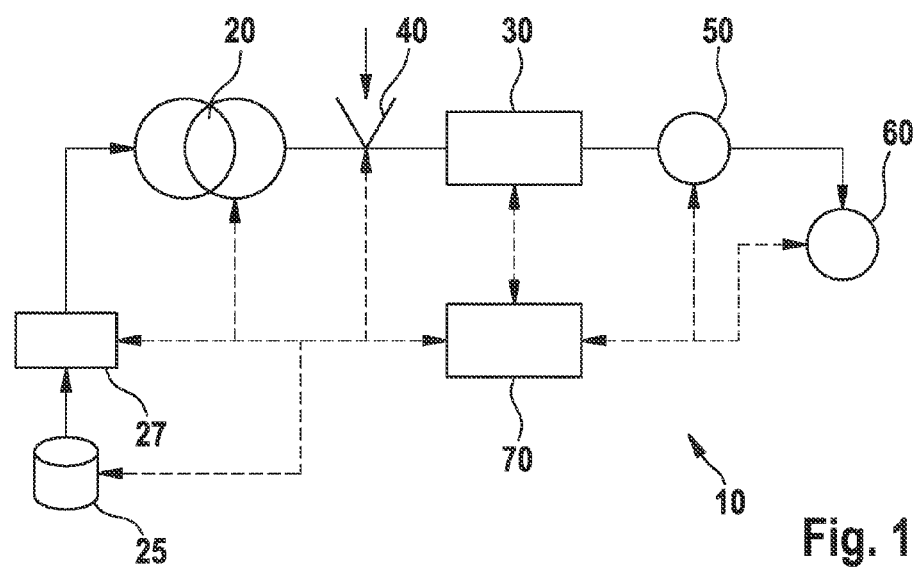
FIG. 1 shows a liquid separation device in accordance with embodiments of the present invention, particularly used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

From the example of FIG. 1, it can be seen that the flow path of the mobile phase typically comprises plural individual components, such as pump 20, separating device 30, sampling unit 40, and detector 50, which are coupled together and which might also be comprised of individual sub-components. Also, fluid conduits, e.g. capillaries, for conducting the fluid are provided as indicated by the solid connections in FIG. 1. Coupling of parts, components and fluid conduits, in particular when using exchangeable or modular parts, is usually provided by using fittings as explained in the introductory part of the description.

For transporting liquid within the liquid separation system 10, typically tubings (e.g. tubular capillaries) are used as conduits for conducting the liquid. Fittings are commonly used to couple plural tubings with each other or for coupling a fluid conduit (e.g. a tubing) to any device. For example, fittings can be used to connect respective fluid conduits to an inlet and an outlet of the separating device 30 in a liquid-sealed fashion. Any of the components in the fluid path (solid line) in FIG. 1 may be connected by fluid conduits e.g. using fittings. While the fluid path after the column 30 is usually at lower pressure, e.g. 50 bar or below, the fluid path from the pump 20 to the inlet of the separating device 30 is under high pressure, currently up to 1200 bar, thus posing high requirements to fluid tight connections.

Due to the high pressure applied in most HPLC applications, pressure sealing of the components in and along the flow path is required. Further, in case of requirement of biocompatibility, it has to be ensured that all surfaces of components (including conduits) along the flow path, which may come in contact with the mobile phase and the sample fluid, are comprised of materials generally considered as being biocompatible, i.e. not releasing ions (e.g. from metal parts) which may contaminate the sample and/or a column packaging material, and/or adversely affect the analysis itself. Accordingly, proper sealing is required to ensure such biocompatibility.

In the following, several representative embodiments of components or devices typically used along the fluid flow path in HPLC as well as corresponding manufacturing methods are described, which provide proper sealing.

In the following, referring to FIG. 2 to FIG. 4, a method of manufacturing a sealing fluidic component 400 (compare FIG. 4) according to a representative embodiment of the invention will be explained.

The basis for the formed sealing fluidic component 400 is a capillary 200 made of fused silica and enclosing a hollow fluid conduit 202 through which a fluid may be conducted. An exterior surface of the capillary 200 is coated with a coating 204 made of PAEK material, i.e. a material being meltable upon increasing its temperature above the melting temperature of PAEK (for instance, a processing temperature of 400° C. or 430° C. may be suitable). In the shown embodiment, the coating 204 is already deposited on the capillary 200 so as to form an integral structure with the capillary 200. Alternatively, it is possible that one or more ring-like members (for instance of PAEK) are slid over an uncoated capillary and having an inner diameter which basically corresponds to an outer diameter of the capillary.

Around the capillary 200 being integrally coated with the coating 204, a tubular metallic sleeve 208 is arranged, preferably in contact to the coating 204. The tubular metallic sleeve 208 serves as a melting heat transfer element for transferring heat provided by an external heat source to the coating 204 of the capillary 200 so as to melt the meltable material, as will be described below in more detail. The tubular metallic sleeve 208 can be made of stainless steel.

Before applying heat to the tubular metallic sleeve 208, the tubular metallic sleeve 208 may be crimped onto the capillary 200 and coating 204 by circumferentially applying pressure to the tubular metallic sleeve 208, thereby plastically deforming it and forcing it against the coating 204 to connect thereby form closure and/or frictional connection. This improves the heat transfer coupling of the arrangement. Then, the so obtained arrangement is inserted into a recess 212 of a molding tool 206. In other words, the molding tool 206 is arranged around an end portion (see reference numeral 300) of the capillary 200, and a part of the recess 212 between a flange face 214 of the structure on the one hand and the molding tool 206 on the other hand remains unfilled. By the recess 212, a shape of the later formed disk-like sealing is defined, since material of the coating 204 advancing forwardly upon being melted can only move into this recess 212. The molding tool 206 can be made of a ceramic material.

Then, a placeholder 210 can be arranged in a space close to the end portion, i.e. at the flange face 214, next to the hollow fluid conduit 202 for maintaining the occupied space free of melted material during a subsequent melting procedure. Thus, after the melting procedure to be described below in more detail, an uninterrupted fluidic path is maintained due to the presence of the placeholder 210 during the remelting procedure from the hollow fluid conduit 202 through the free space within the sealing 402. For example, the placeholder 210 can be made of a ceramic material, of a metallic material or of a plastic having a sufficiently high melting temperature.

Figure 2:
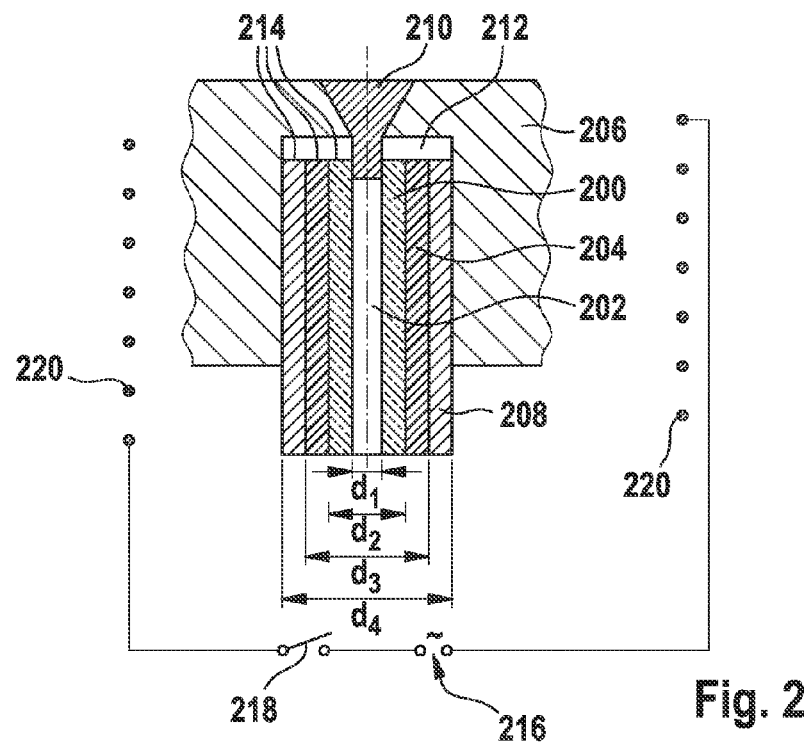
FIG. 2 to FIG. 4 show arrangements obtained during carrying out a method of manufacturing a sealing fluidic component according to a representative embodiment of the invention.

Still referring to FIG. 2, an inner diameter of the hollow fluid conduit 202, d1, can be 50 µm. An outer diameter of the capillary 200, d2, can be 360 µm. An outer diameter, d3, of the coating 204 can be 800 µm. An outer diameter, d4, of the tubular metallic sleeve 208 can be 1600 µm.

As can be taken from FIG. 2, the tubular metallic sleeve 208 is inductively coupled to an alternating current voltage source 216 powering an induction coil 220 (schematically drawn). The alternating current voltage source 216 is capable of generating an alternating current with a frequency of, for instance, 200 kHz to be applied to the induction coil 220 which, in turn, induces eddy currents within the tubular metallic sleeve 208. Hence, when a switch 218 is closed by an operator, a corresponding alternating current is supplied to the induction coil 220 which inductively heats the tubular metallic sleeve 208. Such a contactless heating is preferred over a direct ohmic heating of the sleeve 208 which is however possible as well. The contactless heating advantageously avoids burn-off which may occur at electrodes ohmically connecting the alternating current voltage source 216 to the tubular metallic sleeve 208.

Figure 3:
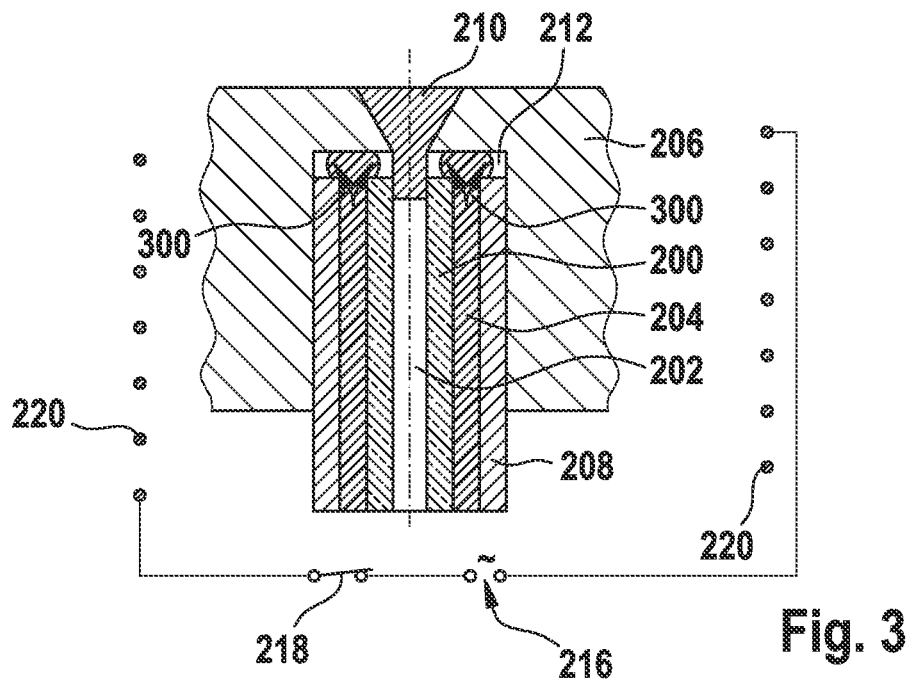

FIG. 3 shows a scenario in which the switch 218 has been closed so that the alternating current provided by the alternating current voltage source 216 is supplied to the induction coil 220 for heating the tubular metallic sleeve 208. As a consequence, the tubular tubular metallic sleeve 208 will be inductively heated and consequently, by heat conduction, the coating 204 of the capillary 200 will also be heated. The amplitude and the frequency of the alternating current supplied by the alternating current voltage source 216 is selected so that the PAEK coating 204 is heated slightly above its melting point, for instance to 360° C. Consequently, the material of the coating 204 is melted and moves forwardly into the recess 212 since this is the only space which remains, and the melting may result in a thermal expansion of the material of the coating 204. This flow in a forward direction may also be supported by applying a force for promoting the forward motion of the melted material (for instance a gravitational force or an externally applied force). As indicated by arrows in FIG. 3, the melted material moves into the recess 212.

When the entire recess 212 is filled with melted PAEK material, the switch 218 can be opened again so that the melted PAEK material solidifies. Then, the placeholder 210 and the molding tool 206 can be removed so that the sealing fluidic component 400 as shown in FIG. 4 is obtained. A ring-like sealing 402 is formed by the resolidified PAEK material arranged at the front face of the capillary 200.

In the following, referring to FIG. 5 to FIG. 7, a method of manufacturing a sealing fluidic component 700 (compare FIG. 7) according to another representative embodiment of the invention will be explained.

Figure 5:
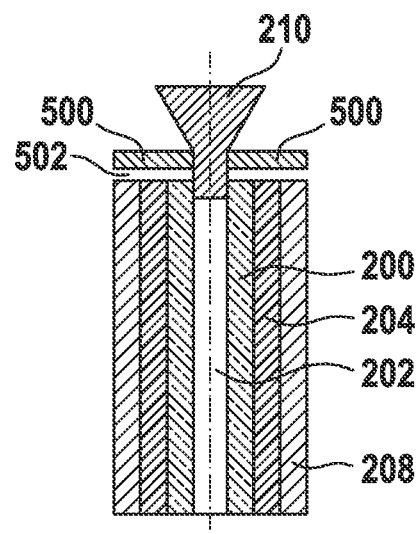
FIG. 5 to FIG. 7 show other arrangements obtained during carrying out a method of manufacturing a sealing fluidic component according to another representative embodiment of the invention.

As can be taken from FIG. 5, no molding tool 206 needs to be provided in the described embodiment, although possible. Furthermore, a disk-like sealing member 500 is provided additionally which is arranged, separated by a gap 502 from the tubular arrangement of capillary 200, coating 204 and tubular metallic sleeve 208.

Figure 6:
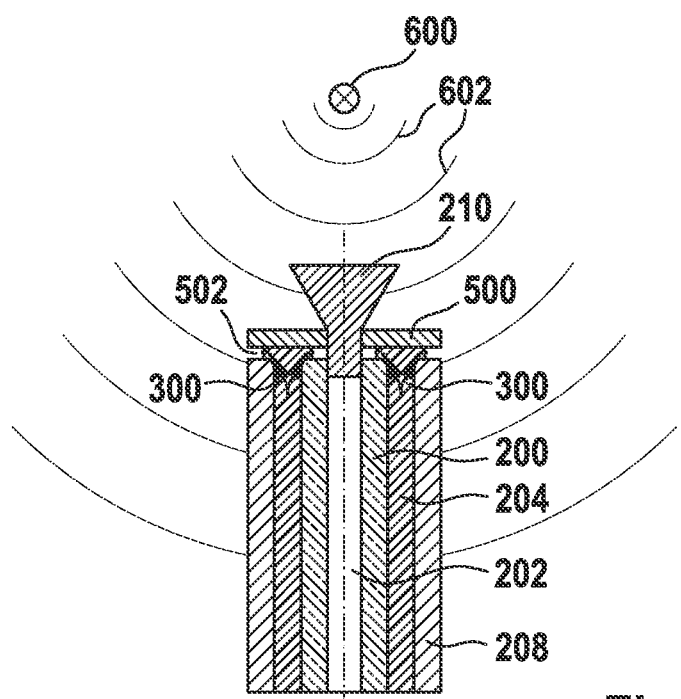

As can be taken from FIG. 6, melting of material of the coating 204 is initiated by an infrared source 600 which irradiates infrared radiation 602 onto the arrangement described referring to FIG. 5. Due to the thermal radiation, the material of the coating 204 is selectively heated and liquefied, since its melting temperature (PAEK material) is lower than the melting temperature of the fused silica of the capillary 200 and the titanium material of the tubular metallic sleeve 208.

Figure 7:
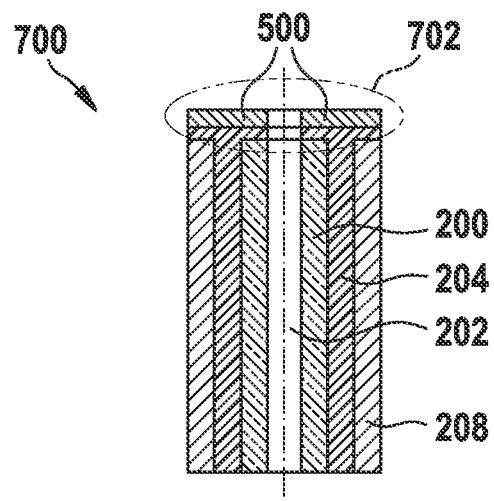

In the embodiment of FIG. 5 to FIG. 7, the tubular metallic sleeve 208 is optional and is provided to improve the thermal exchange between the infrared radiation 602 and the PAEK material of the coating 204. However, in other embodiments, the tubular metallic sleeve 208 can be omitted, since the thermal interaction between the radiation 602 and the coating 204 may be sufficient to initiate melting of the coating 204 particularly at the end portion thereof facing the electromagnetic infrared source 600. As can be taken from arrows in FIG. 6, the melted material may be forced into the gap 502 to thereby fill the gap 502 at least partly. Particularly when the surface of the PAEK ring 500 has been functionalized by plasma treatment or the like beforehand, the melted material of the coating 204 bonds or adheres to the ring 500 to form an integral structure.

As can be taken from FIG. 7, after resolidifying the PAEK material of the coating 204, the sealing 702 is formed from the remelted material of the coating 204 and the material of the annular ring 500 (which remains solid during the entire procedure).

Figure 7A:
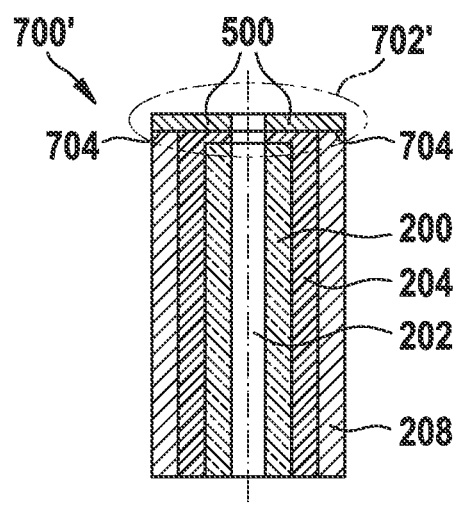
FIG. 7A shows a sealing fluidic component according to another representative embodiment of the invention manufactured in accordance with still another method similar to the one described referring to FIG. 5 to FIG. 7.

FIG. 7A shows an alternative sealing fluidic member 700' which is very similar to the sealing component 700 but differs in the fact that the tubular metallic sleeve 208 and the annular ring 500 are integrally formed, for instance adhered to one another in an annular connection region 704. Hence, the capillary 200 coated with the coating 204 and forming another integral structure may be slid in an interior conduit of the arrangement of tubular metallic sleeve 208 and adhered annular ring 500. Subsequently, a heating procedure may be carried out which then forces material of the coating 204 into the gap formed close to the annular connection region 704 of annular ring 500 and tubular metallic sleeve 208. This results in the sealing 702' shown in FIG. 7A.

Figure 4:
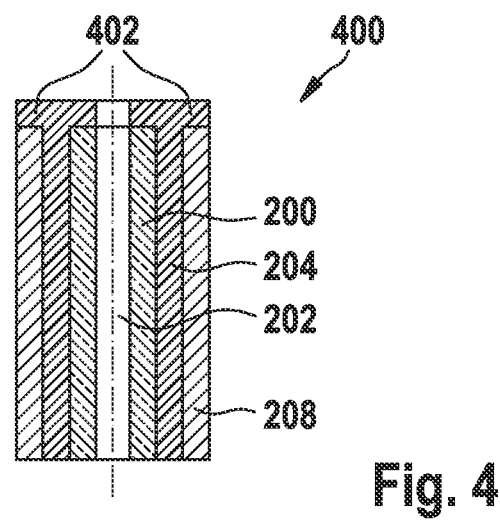
Figure 8:
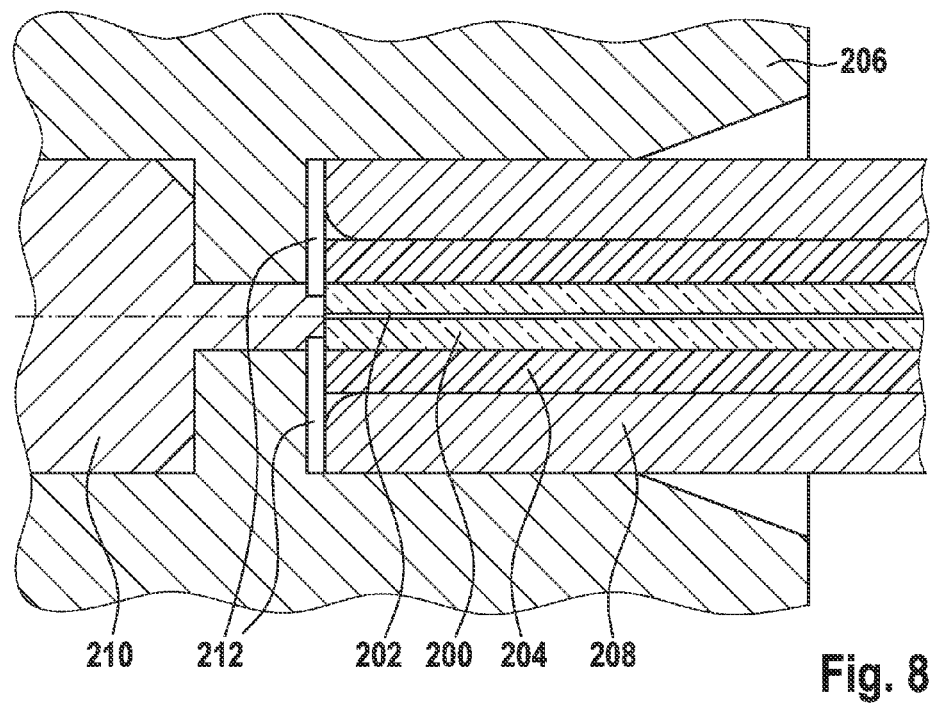
FIG. 8 shows a cross-sectional view of an unmelted tip in a tooling used for forming a sealing at a front face of a coated capillary according to a representative embodiment of the invention.

FIG. 8 is a cross-sectional view of a semi-finished component based on which a sealing fluidic component similar to the one shown in FIG. 4 can be formed. Prior to the melting of material of the coating 204 of the capillary 200, there is still a recess 212 in which later melted and resolidified material of the coating 204 can be accommodated.

Figure 9:
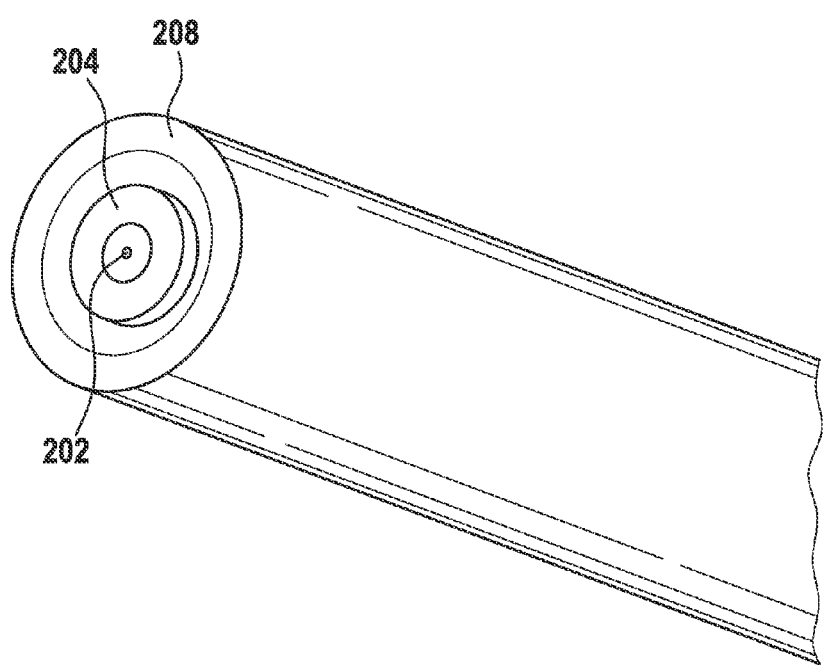
FIG. 9 shows a perspective view of the unmelted tip of FIG. 8.

FIG. 9 shows a perspective view of the arrangement inserted into the molding tool 206 in FIG. 8.

Figure 10:
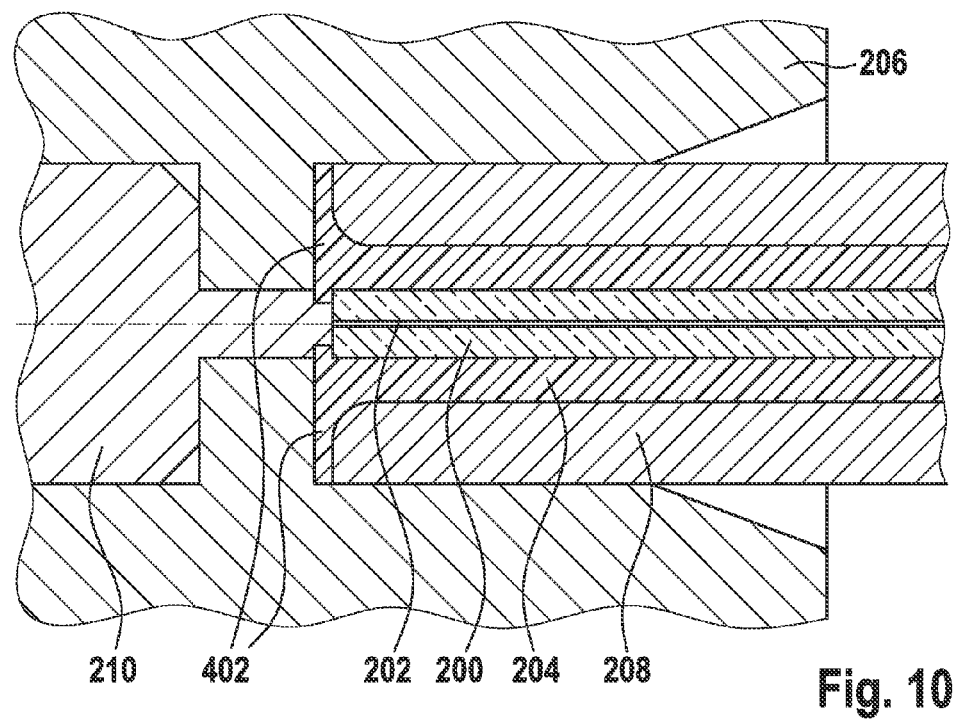
FIG. 10 is a cross-sectional view of a remelted tip in a tooling as obtained during carrying out a method according to a representative embodiment of the invention.

FIG. 10 shows a cross-sectional view of a sealing fluidic component (still within a tooling, i.e. molding tool 206) which can be obtained starting from FIG. 8 and subsequently filling the recess 212 with remelted material of the coating 204.

Figure 11:
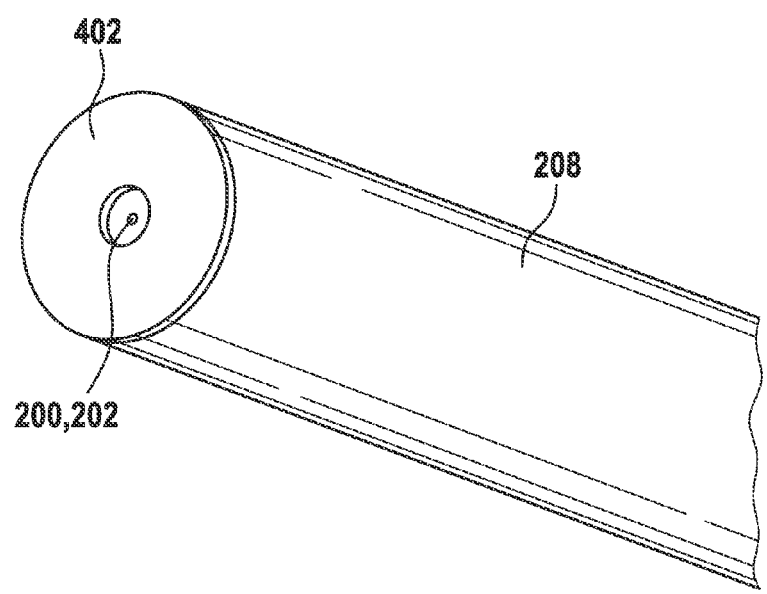
FIG. 11 is a perspective view of a remelted tip of FIG. 10.

Corresponding to FIG. 10, FIG. 11 is a perspective view of the sealing fluidic component with sealing 402 covering the entire front face of the tubular metallic sleeve 208.

Figure 12:
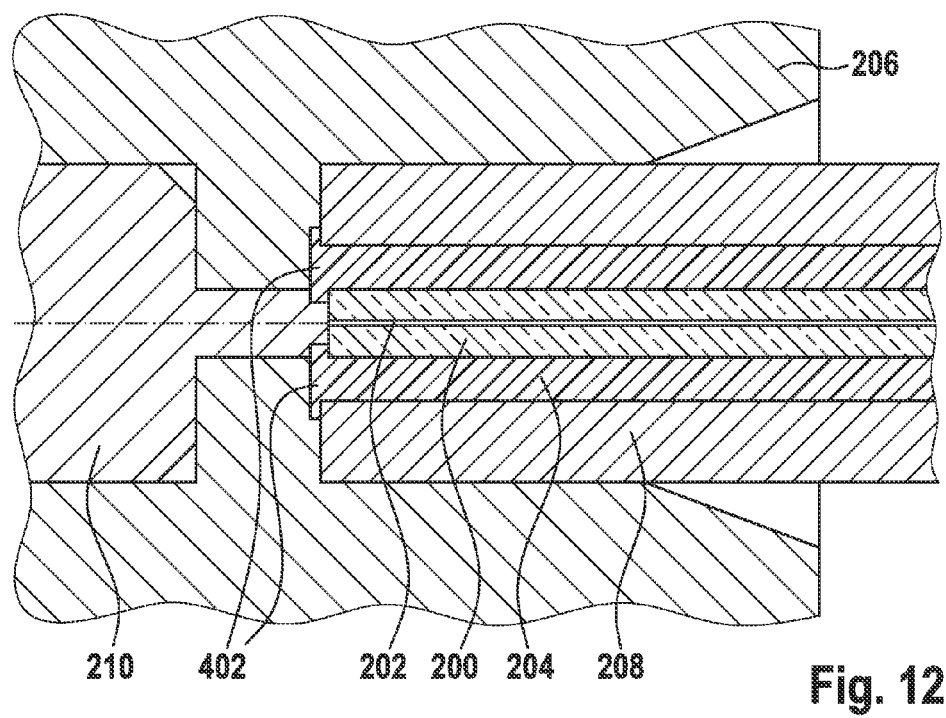
FIG. 12 shows a cross-sectional view of a remelted tip in a tooling as obtained after having carried out a method according to a representative embodiment of the invention.

FIG. 12 shows a perspective view of an arrangement similar to FIG. 10 after remelting and resolidifying, i.e. after filling recess 212 with PAEK material of the coating 204. However, in the embodiment of FIG. 12, the sealing element 402 covers the front face of the tubular metallic sleeve 208 only partially. In contrast to this, remelting and resolidifying the material of the coating 204 starting from FIG. 8 will result in an annular sealing which covers both the coating 204 and the tubular metallic sleeve 208 over the entire flange face (see FIG. 10).

Figure 13:
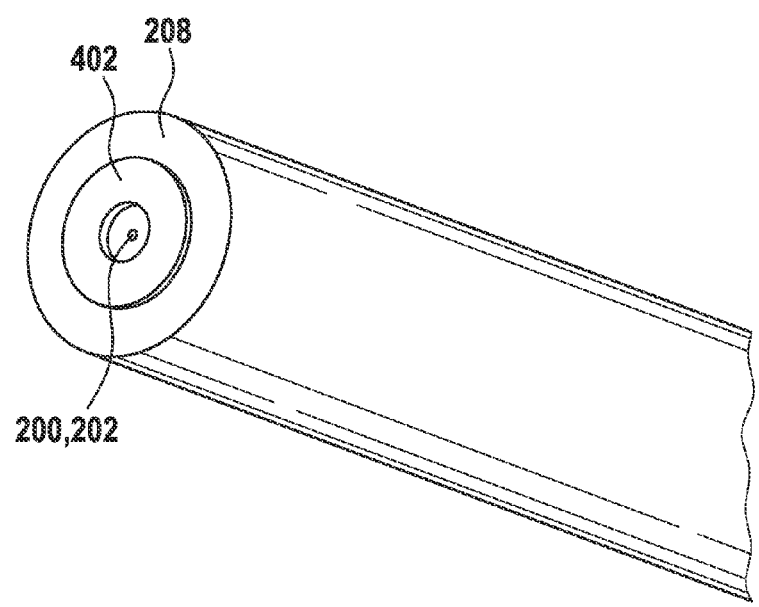
FIG. 13 is a perspective view of a coated capillary provided with a front face sealing according to a representative embodiment of the invention.

FIG. 13 shows a perspective view of the sealing fluidic component of FIG. 12 and shows also that the sealing 402 protrudes from a front face of the tubular sleeve 208.

Figure 14:
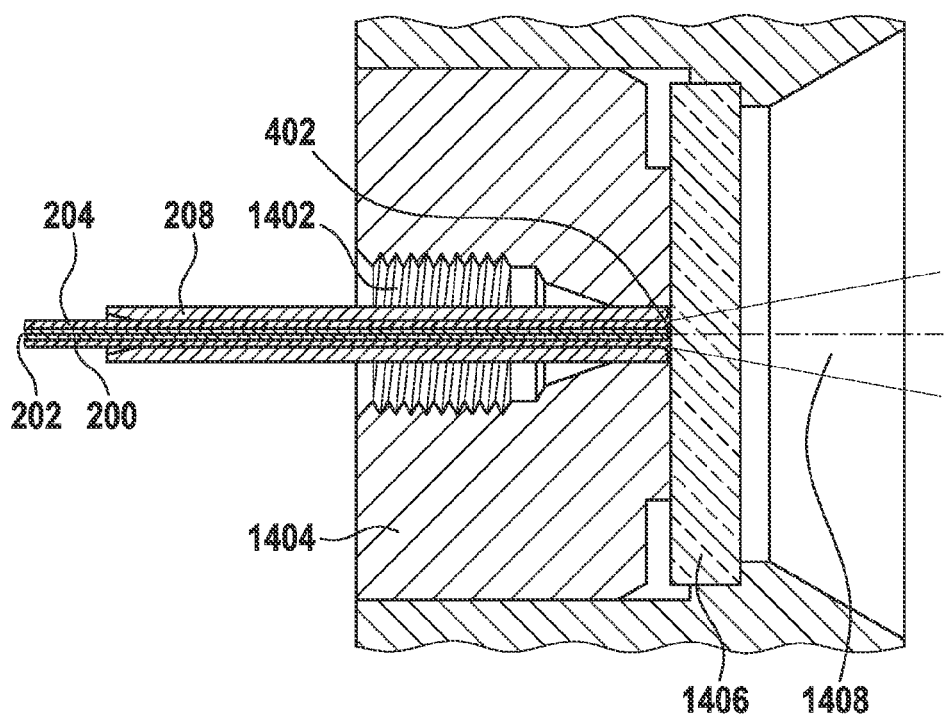
FIG. 14 is a cross-sectional view of a capillary having a front sealing according to a representative embodiment of the invention being heated by laser radiation which is directed towards a front face of the sealing through a glass plate.

FIG. 14 illustrates further processing based on a readily formed sealing fluid member according to a representative embodiment.

FIG. 14 shows a capillary 200 with a coating 204 and a crimped tubular metallic sleeve 208 already after having formed a sealing 402 at a front face of such an arrangement. This arrangement has been inserted in a housing 1402 for instance a metallic material having an external thread cooperating with an internal thread formed within a housing 1404 in which the arrangement with the housing 1402 has been screwed. Furthermore, a transparent glass plate 1406 or any other optically transparent substrate can be arranged so that a surface of the transparent glass plate 1406 faces and contacts a front surface of the sealing 402. Although not shown in detail in FIG. 14, the surface of the transparent glass plate 1406 facing the sealing 402 may have a surface profile or pattern. Thus, by pressing the transparent glass plate 1406 against the sealing 402, a contact force is applied to these two surfaces. Subsequently, a laser source (not shown in FIG. 14) or any other electromagnetic radiation source is activated so as to irradiate an electromagnetic radiation beam 1408, for instance a laser beam, focused onto the two opposing surfaces of the sealing element 402 and transparent glass plate 1406. This causes the material of the sealing 402 to be again melted, wherein subsequent resolidification of the material of the sealing 402 will result in the formation of corresponding profiles on the faces of the sealing 402 and the transparent glass plate 1406. Thus, a patterning of the surface of the sealing 402 is possible even after having formed the sealing 402.

Figure 15:
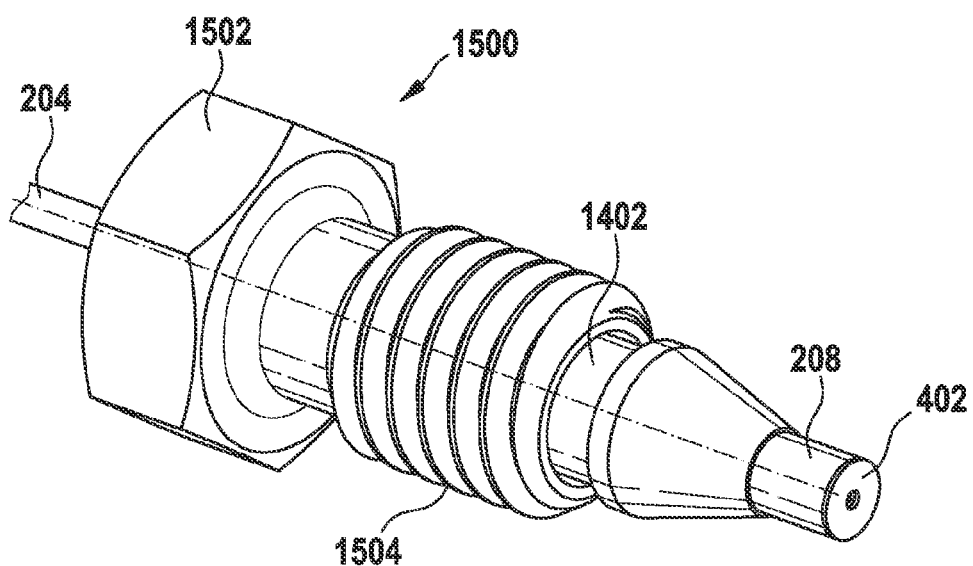
FIG. 15 is a perspective view of a fitting according to a representative embodiment of the invention.

FIG. 15 shows a perspective view of a fitting 1500 which, additionally to above described components, has a screw head 1502 and an external thread 1504.

Figure 16:
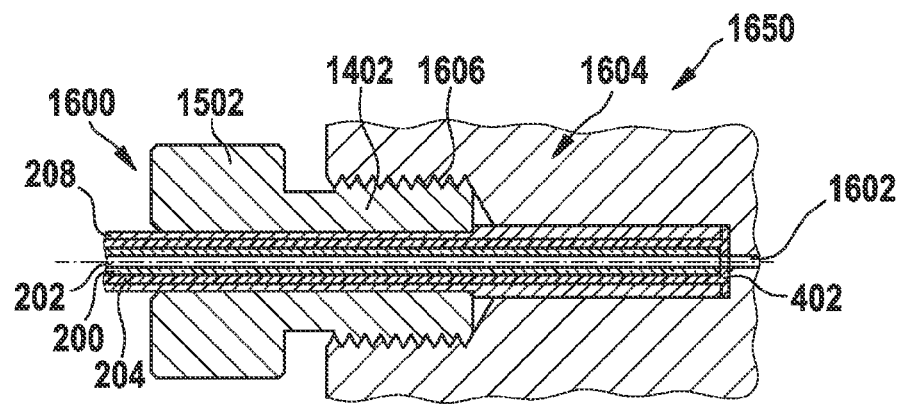
FIG. 16 is a cross-sectional view of a fitting screwed in a housing according to a representative embodiment of the invention.

FIG. 16 shows a fluidic device 1650 having a fitting 1600 formed according to a representative embodiment of the invention. A screw head 1502 and housing 1402 are arranged around the structure of capillary 200, hollow fluid conduit 202, coating 204, tubular metallic sleeve 208 and sealing element 402 as described above. This fitting 1600 is screwed in a connector component 1604 (see two cooperating threads, compare reference numeral 1606) to provide for a screwing connection. Thus, the capillary 200 will be brought in sealing alignment with a connected fluid conduit 1602 in connector component 1604.

Figure 17:
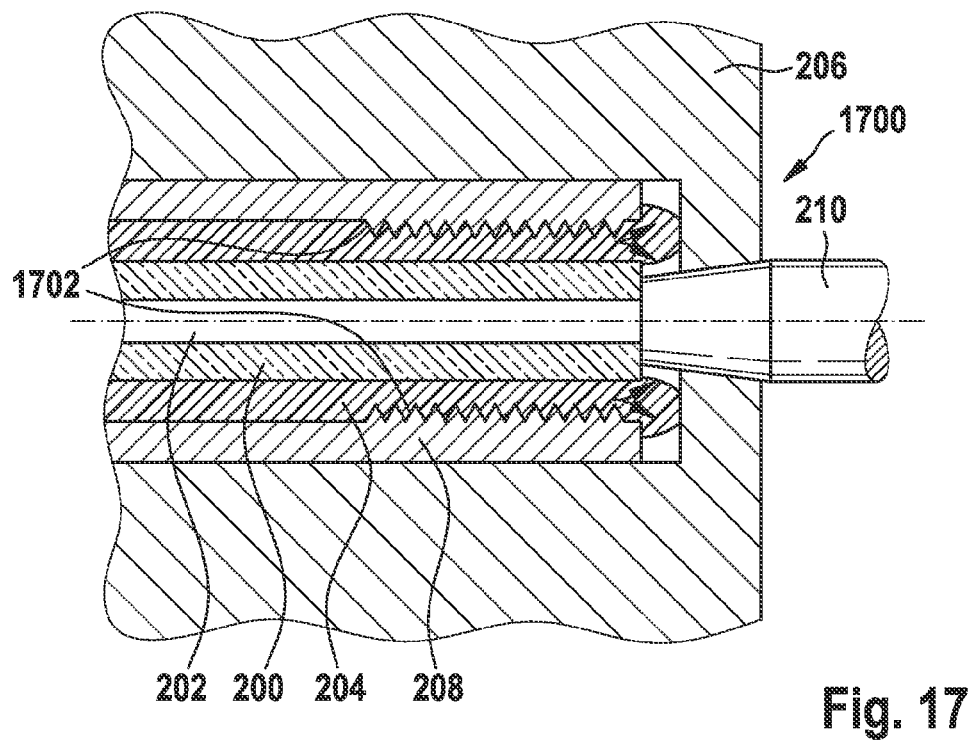
FIG. 17 shows an arrangement which illustrates the process of forming a sealing, wherein a partially threaded sleeve is used.

FIG. 17 shows an arrangement 1700 (similar to FIG. 3) which illustrates the process of forming a sealing. In the arrangement 1700, an internal thread 1702 is formed exclusively in a front section of an inner surface of a tubular metallic sleeve 208, the threaded front section being directly adjacent to the sealing to be formed, whereas a rear section of the inner surface of the tubular metallic sleeve 208 is smooth and free of a thread. During mounting, the tubular metallic sleeve 208 is turned on the coating 204 of the capillary 200. This ensures a proper thermal coupling as well as provides a form closure between capillary 200 and tubular metallic sleeve 208.

Figure 18:
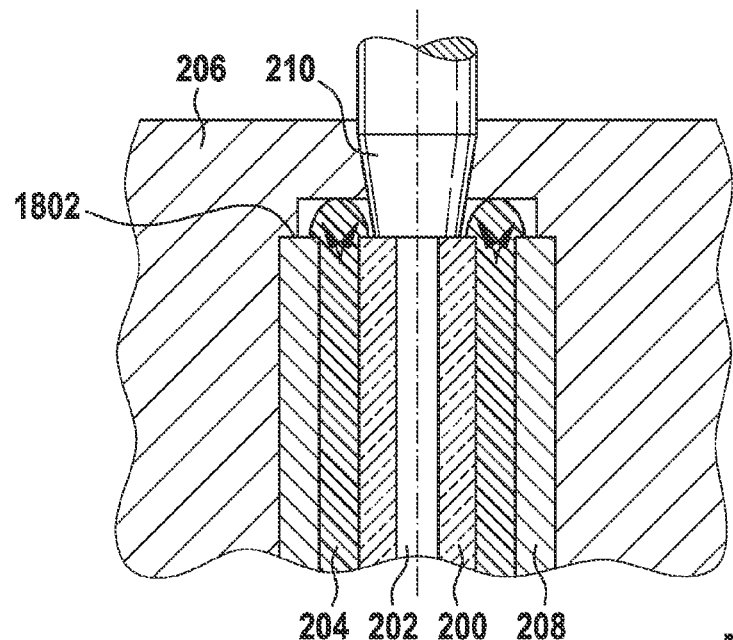
FIG. 18 show an arrangement which illustrates the process of forming a sealing similar to FIG. 12 with a step between sleeve and sealing, wherein a placeholder is placed outside of the capillary.

FIG. 18 shows an arrangement similar to FIG. 12 which illustrates the process of forming a sealing in which a placeholder 210 is placed outside of the capillary 200. In this embodiment, the placeholder 210 is pushed towards an end opening of the capillary 200 to close it and to prevent clogging of the capillary 200 during formation of the sealing. A step 1802 between tubular metallic sleeve 208 and the sealing to be formed is beneficial for the positioning of the tubular metallic sleeve 208. The tubular metallic sleeve 208 can be pressed against it during remelting and thereby precisely maintains position with respect to the capillary 200 which is in an abutting condition as well.

Figure 19:
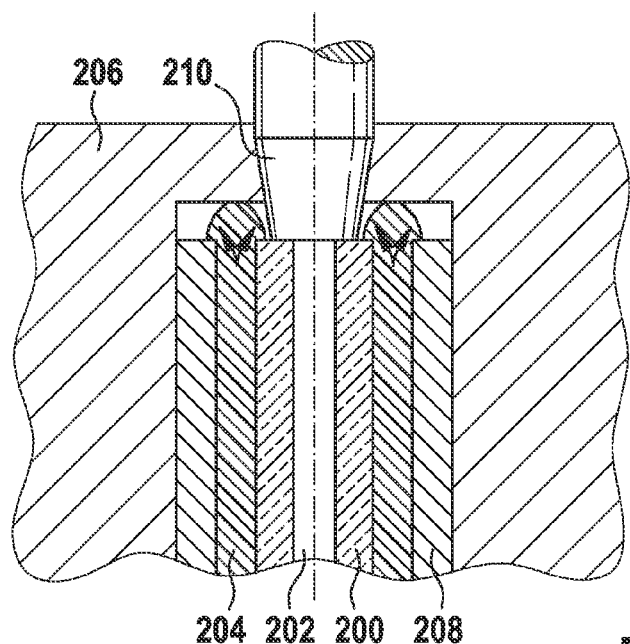
FIG. 19 shows an arrangement which illustrates the process of forming a sealing similar to FIG. 10 without a step between sleeve and sealing, wherein a placeholder is placed outside of the capillary.

FIG. 19 shows an arrangement similar to FIG. 10 which illustrates the process of forming a sealing in which a placeholder 210 is placed outside of the capillary 200. Also in this embodiment, the placeholder 210 is pushed towards an end opening of the capillary 200 to close it and to prevent clogging of the capillary 200 during formation of the sealing.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

While example embodiments are disclosed herein, one of ordinary skill in the art appreciates that many variations that are in accordance with the present teachings are possible and remain within the scope of the appended claims. The invention therefore is not to be restricted except within the scope of the appended claims.

I claim:

1. A method of manufacturing a sealing fluidic component, the method comprising:
providing an arrangement comprising a capillary enclosing a fluid conduit and comprising an exterior surface at least partially coated with a coating of a meltable material, and a melting heat transfer element coaxially surrounding the coating;

placing at least an end portion of the capillary in a molding tool such that the molding tool is arranged around at least part of the melting heat transfer element;

melting the meltable material of the coating at least at the end portion of the capillary, wherein the end portion terminates at a front face of the capillary, and wherein melting the meltable material comprises transferring heat to the coating via the melting heat transfer element;

resolidifying the melted material to thereby form, at the end portion, a sealing integral with the coating and constituted at least partially by the meltable material, wherein resolidifying forms the sealing fluidic component comprising the sealing; and after resolidifying, removing the sealing fluidic component from the molding tool, wherein:

the sealing spans at least a portion of the front face without interrupting a fluidic path through the fluid conduit; and the sealing fluidic component is configured to be mechanically and fluidically coupled to a receiving space in a connector component comprising a further fluid conduit.

2. The method according to claim 1, wherein the capillary is integrally coated with the coating.

3. The method according to claim 1, wherein the coating is provided as at least one annular member being separate from the capillary and being slid over the capillary.

4. The method according to claim 1, wherein the method further comprises, between the melting and the resolidifying:

guiding at least a part of the melted material forwardly beyond the end portion of the capillary while maintaining a continuous connection between the forwarded material and remaining material of the coating.

5. The method according to claim 1, wherein the method further comprises, prior to the resolidifying:

guiding at least a part of the melted material forwardly beyond the end portion, such that the sealing that spans at least the portion of the front face comprises a disk-like sealing of the forwardly advancing melted material integral with the coating.

6. The method according to claim 5, wherein the molding tool comprises a recess defining at least partially a shape of the disk-like sealing formed within the recess by the forwardly advancing melted material.

7. The method according to claim 1, wherein the method further comprises applying pressure to at least a part of a circumference of the melting heat transfer element to thereby press the melting heat transfer element onto the coating.

8. The method according to claim 1, wherein the melting heat transfer element has a composition selected from the group consisting of: a metal, stainless steel, and titanium.

9. The method according to claim 1, wherein the method further comprises, prior to the melting:

arranging a placeholder in a space at the end portion next to the fluid conduit for maintaining the space free of melted material to thereby establish a continuous fluidic path from the fluid conduit through the free space within the sealing.

10. The method according to claim 1, wherein the melting comprises heating the meltable material to a temperature higher than a melting temperature of the meltable material but lower than a melting temperature of a material of the capillary.

11. The method according to claim 1, wherein the melting comprises at least one of the group consisting of: inductively heating the melting heat transfer element; inductively heating an electrically conductive material thermally coupled to the coating; supplying thermal energy to the coating; irradiating the coating by electromagnetic radiation; and irradiating the coating by infrared radiation.

12. The method according to claim 1, wherein the meltable material comprises at least one of the group consisting of polyetheretherketone, polyetherketone, polyetherketoneketone, polyetheretherketoneketone, and polyetherketoneetherketoneketone.

13. The method according to claim 1, wherein the capillary has a composition selected from the group consisting of: a metal, a plastic, and fused silica.

14. The method according to claim 1, wherein the fluid conduit has a cross section selected from the group consisting of: a circular cross section, an elliptical cross section, a polygonal cross section, and a rectangular cross section.

15. The method according to claim 1, further comprising:

pressing the sealing against a patterned surface portion of a substrate being at least partially transparent for electromagnetic radiation;

irradiating the sealing through the patterned surface portion of the substrate with electromagnetic radiation to thereby remelt material of the sealing so that the remelted material is patterned inverse with respect to the patterned surface portion; and subsequently resolidifying the remelted material.

16. The method according to claim 1, wherein the melting heat transfer element comprises a front face surrounding the front face of the capillary, and the sealing spans at least a portion of the front face of the melting heat transfer element.

17. The method according to claim 1, wherein the melting heat transfer element is a metallic cylindrical sleeve.

* * * * *